United States Patent [19]

Wiebusch

[11] 4,323,081

[45] Apr. 6, 1982

[54] PACING LEAD

[75] Inventor: Wendy A. Wiebusch, White Bear Lake, Minn.

[73] Assignee: Medtronic, Inc., Minneapolis, Minn.

[21] Appl. No.: 164,421

[22] Filed: Jun. 30, 1980

[51] Int. Cl.³ .............................................. A61N 1/04
[52] U.S. Cl. ................................. 128/785; 128/419 P
[58] Field of Search .................... 128/419 P, 784, 785, 128/786

[56] References Cited

U.S. PATENT DOCUMENTS

| | | | |
|---|---|---|---|
| 3,367,339 | 2/1968 | Sessions | 128/786 |
| 3,650,276 | 3/1972 | Burghele et al. | 128/784 |
| 3,737,579 | 6/1973 | Bolduc | 128/785 |
| 3,749,101 | 7/1973 | Williamson | 128/786 |
| 3,978,865 | 9/1976 | Trabucco | 128/785 |
| 4,026,303 | 5/1977 | Babutai | 128/785 |

Primary Examiner—William E. Kamm
Attorney, Agent, or Firm—John L. Rooney; Joseph F. Breimayer; Carl A. Forest

[57] ABSTRACT

Pacing lead including an elasticized snap-on sleeve integral with a fixation pad for covering and protecting a tip of an electrode, and which is designed for either ventricular or atrial pacing. The electrode includes a U-shaped mid-portion, and extends into and across a hole in the fixation pad. The bottom of the U-shaped portion is recessed slightly below the hole to a position slightly below the lower surface of the elasticized fixation pad. The pacing lead is intended for permanent epicardial pacing, includes a one piece design, provides for easy insertion, is acutely removable, is intended for long-term fixation and acute fixation, and has a low profile suitable for either ventricular or atrial pacing.

12 Claims, 4 Drawing Figures

U.S. Patent  Apr. 6, 1982  4,323,081
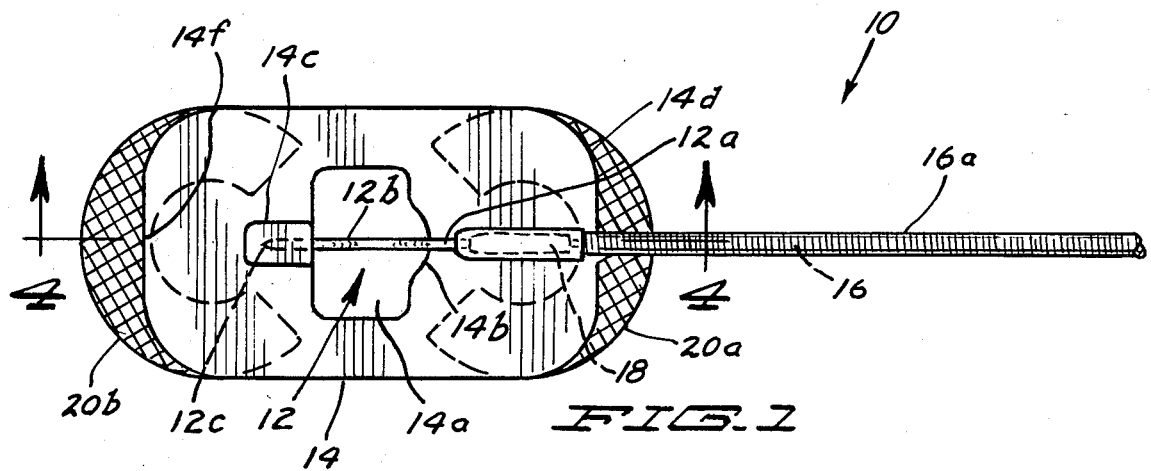
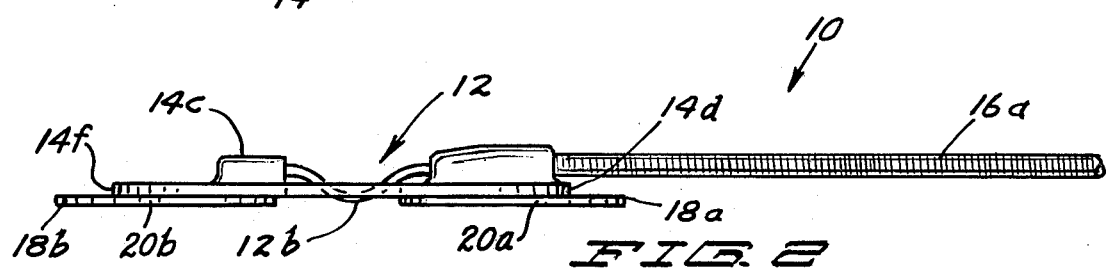
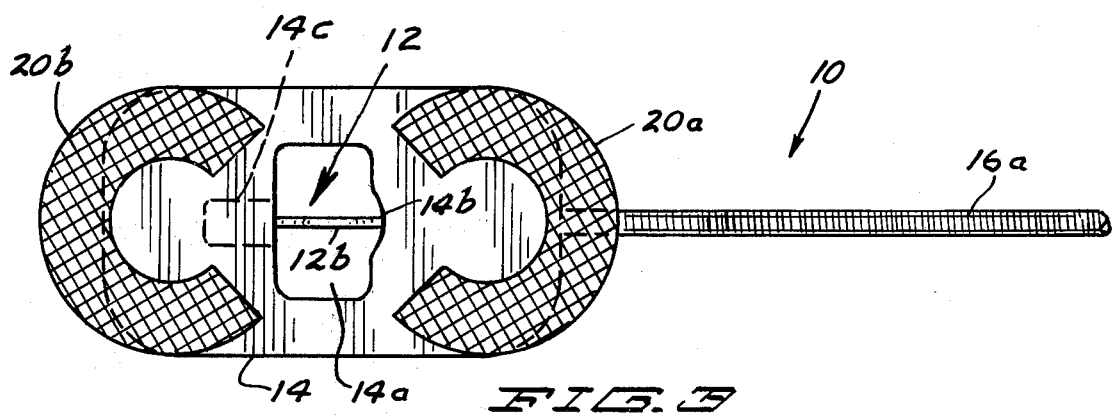
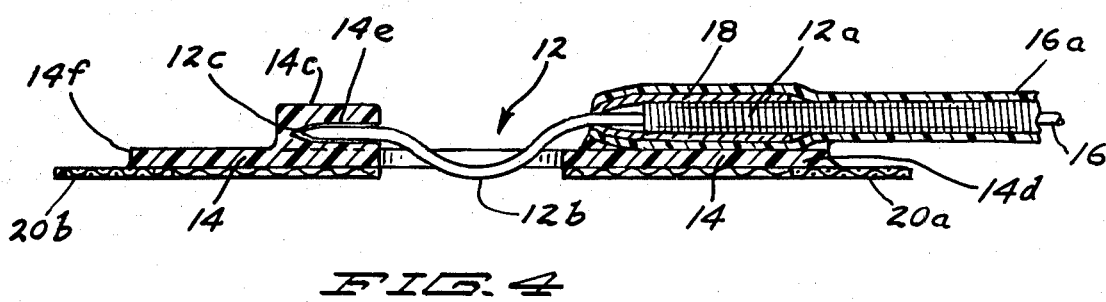

PACING LEAD

BACKGROUND OF THE INVENTION

1. Field of the Invention

The present invention relates to a surgical electrical applicator, and more particularly, pertains to an epicardial sutureless pacing lead.

2. Description of the Prior Art

Prior art epicardial leads have usually had to be sutured into position which has been difficult for medical personnel in applying the lead to the epicardial tissue. The suturing of the epicardial lead presents a surgical problem in the application of an electrode of the pacing lead to the epicardial tissue of the heart. The sutured epicardial pacing leads have sometimes been considered less than desirable and satisfactory in the application of the sutured electrode into the epicardial tissue of the heart.

Other prior art epicardial leads have required tools for application of the pacing electrode into the epicardial tissue of the heart. The tools required surgical manipulation by medical personnel applying the electrode to the epicardial tissue of the heart.

The application of prior art pacing electrodes required special forceps or special application tools. Numerous turns of the electrode for affixation on implant required medical personnel who had adept dexterity in the application of the pacing electrode. Also, the pacing electrode required additional tools which also required more time for application of the electrode to the epicardial tissue of the heart, and also required a large working area on the heart of the individual patient for the application of the pacing electrode.

Finally, the prior art pacing leads had little or no stretch or flexibility within the electrode and the lead itself, sometimes resulting in high chronic thresholds. Chronic results were sometimes less than desirable due to the lack of stretch of the pacing lead, especially between the pacing electrode and the distal end of the lead itself. Also the prior art pacing electrodes require physical height between the epicardial tissue and the thoracic cavity, not only during application of the pacing electrode, but for subsequent pacing of the heart.

The present invention overcomes the disadvantages of prior art epicardial pacing leads by providing a sutureless epicardial pacing lead which requires no stab wound or sutures for electrode placement and support, and a pacing electrode which can be secured to the heart by gently pushing the tip of the electrode into the epicardial tissue and subsequently securing the electrode with the elasticized snap-on end sleeve of the fixation pad thereby covering and protecting the electrode tip.

SUMMARY OF THE INVENTION

The purpose of the present invention is to provide a sutureless epicardial pacing lead which is safe and easy in application to epicardial tissue of the heart, and provides a low-profile, light weight electrode head with a small flexible lead behind the electrode where the tip of the electrode is covered after being pushed in and through the epicardial tissue with an elasticized snap-on sleeve on the fixation pad for subsequent engagement over the tip of the electrode of the pacing lead.

According to one embodiment of the present invention, there is provided an epicardial sutureless unipolar pacing lead including a forward-facing electrode having a tip in axial alignment with the end of the electrode and including a U-shaped indentation in a substantially midportion of the electrode, a flexible elasticized fixation pad having a substantially centered hole for receiving the U-shaped indentation in the electrode where the bottom of the U-shaped portion extends slightly below the fixation pad, the end of the electrode affixed to one side of the hole in the fixation pad and an elasticized snap-on sleeve on the other side of the hole in the fixation pad opposing the end of the electrode, an insulated coiled conductor having a terminal pin at a proximal end and a distal end of the diameter which accepts the end of the electrode, an attachment sleeve for attaching the coiled conductor over the end of the electrode and insulation over the attachment sleeve securing the distal end of the coiled conductor to the fixation pad with medical adhesive whereby the opposing end of the fixation pad having the snap-on sleeve is pulled up and over the attachment sleeve of the electrode whereupon the tip of the electrode is pushed into and out through the epicardial tissue, and then the snap-on sleeve on the elasticized fixation pad is pulled over and snapped into place on the tip of the electrode thereby providing for implantation of the pacing electrode in the epicardial tissue of the heart and securing of the electrode in the epicardial tissue.

The pacing electrode can be used in either ventricular pacing or atrial pacing depending upon the specific placement of the pacing electrode.

A significant aspect and feature of the present invention is a sutureless, epicardial, unipolar pacing lead which requires no stab wound or sutures for electrode placement of the U-shaped electrode in and through the epicardial tissue. The electrode is secured in the epicardial tissue by gently pushing the tip in and through the epicardial tissue and is subsequently secured in place by snapping on a sleeve over the tip of the electrode.

Another significant aspect and feature of the present invention is a sutureless epicardial pacing lead which provides better chronic results and is less traumatic to the patient. The lead, due to its unique construction, reduces high chronic thresholds, and the reason is that there is a certain amount of flex and stretchability provided by the configuration of the electrode head and the low profile coiled conductor attached to the electrode which also results in less pericardial rub. The flexible fixation pad and the coiled conductor also provide a certain amount of flexibility and stretch thus reducing high chronic thresholds.

Another significant aspect and feature of the present invention and most importantly is a sutureless epicardial pacing lead which is easy to install and includes a flexible base pad designed for long term and acute fixation. The electrode is acutely removable at a later time for whatever reason.

BRIEF DESCRIPTION OF THE DRAWINGS

Other objects and many of the attendant advantages of this invention will be readily appreciated as the same becomes better understood by reference to the following detailed description when considered in connection with the accompanying drawing, in which like referencce numerals designate like parts throughout the FIGURES thereof and wherein:

FIG. 1 illustrates a top plan view of a sutureless epicardial pacing lead of the present invention;

FIG. 2 illustrates a side view of the present invention;

FIG. 3 illustrates a bottom view of the present invention; and

FIG. 4 illustrates a sectional view taken along line 4—4 of FIG. 1.

DESCRIPTION OF PREFERRED EMBODIMENT

FIG. 1, which illustrates a top plan view of a sutureless epicardial pacing lead 10, the present invention, shows the pacing lead 10 including a forward-facing in-line electrode 12 including a proximal end 12a as also illustrated in FIG. 4, a U-shaped junction 12b in the substantially mid-portion of the electrode 12 which extends slightly below a lower surface of a fixation pad 14 and a sharp pointed electrode tip 12c as also illustrated in FIG. 4. The flexible elasticized fixation pad 14 is composed of polyether urethane elastomer or like material having an elongated rectangular shape with slightly rounded corners including a hole 14a having a semicircular indentation 14b adjacent to the end 12a of the electrode 12, and a snap-on sleeve 14c adjacent distal end 14f of fixation pad 14 as later described in detail. A multi-filar coiled pacing conductor coil 16 such as trifilar or quadrafilar silver MP35N Drawn-Brazed-Strand (DBS) composite wire including insulation 16a such as urethane or silicone rubber by way of example and for purposes of illustration only connects to proximal end 12a of electrode 12 with an attachment sleeve 18 swaged over the coiled conductor 16 which engages over proximal 12a of electrode 12 as illustrated in FIG. 4. The attachment sleeve 18 which engages over the end of coiled conductor 16 which likewise engages over the end of the electrode 12 secures together to the end 14d of the elasticized fixation pad 14 by affixing the insulation 16a to the fixation pad 14 with a suitable medical adhesive or like material. Opposing surgical mesh patches 20a and 20b having rounded circumferential portions surround the elasticized fixation pad about the hole 14a and are affixed to the fixation pad 14 with any suitable medical adhesive by way of example and for purposes of illustration only.

FIG. 2, which illustrates a side view of the epicardial pacing lead 10, shows numerals which correspond to those elements previously described. Particular attention is drawn to the shape of the electrode 12, specifically the U-shaped portion 12b in the substantially mid-portion of the electrode 12 and the protruding of the lower portion of the U-shaped portion below the bottom of the fixation pad 14. The snap-on sleeve 14c is clearly illustrated as being in axial alignment with the distal end of the coiled conductor 16 and proximal end 12a of the electrode 12 at the opposing end of the fixation pad 14.

FIG. 3 illustrates a bottom view of the pacing lead 10 of the present invention where all numerals correspond to those elements previously described.

FIG. 4, which illustrates a sectional view taken along line 4—4 of FIG. 1, shows in particular detail the pacing lead 10 of the present invention including the electrode 12, the elasticized fixation pad 14 including the snap-on sleeve 14c having an internal hole 14e to accommodate the sharp pointed tip 12c of the electrode 12, the coiled conductor 16, the attachment sleeve 18, and the surgical mesh patches 20a and 20b. All other numerals correspond to those elements previously described. Particular attention is again drawn to the specific position of the U-shaped mid-portion 12b to the fixation pad 14.

PREFERRED MODE OF OPERATION

The application of the sutureless epicardial unipolar pacing lead 10 which is body implantable is performed by first providing access to the epicardial tissue, either by keyhole implantation or through the thoracic cavity of the patient.

The electrode 12 can be slid into position without the need of an insertion tool, and is inserted through the epicardial tissue and out the other opposing side of the insertion point with the U-shaped mid-portion 12b of the electrode 12 remaining in the epicardial tissue. During insertion, the end 14f of the fixation pad 14 is pulled back to and substantially over in alignment with the end 14d of the fixation pad 14. After insertion of the electrode through and out of the epicardial tissue, the distal end 14f of the fixation pad 14 is released and the snap-on sleeve is engaged over the sharp pointed tip 12c whereby the hole 14e of the snap-on sleeve 14c engages over the sharp pointed tip 12c.

After implantation, surgical mesh patches 20a and 20b provide for fibrous ingrowth about the epicardial tissue.

In the event that the pacing lead 10 including the electrode 12 is removed, the electrode 12 can be carefully removed by back-stepping as previously described by disengaging the sharp pointed tip 12c from the snap-on sleeve 14c of the fixation pad 14, pulling the electrode out through the epicardial tissue, and eliminating the surgical mesh patches 20a and 20b which are engaged by fibrous ingrowth to the epicardial tissue.

Various modifications can be made to the pacing lead 10 of the present invention without departing from the apparent scope thereof.

Having thus described the invention, what is claimed is:

1. A body implantable lead comprising:
   a conductor having a distal end;
   an insulating sheath having a distal end fixedly attached to and covering said conductor;
   an electrode having proximal and distal ends and having said proximal end fixedly attached to said distal end of said conductor; and
   electrode support means fixedly attached to said distal end of said insulating sheath for disengaging attachment to said distal end of said electrode.

2. A body implantable lead according to claim 1 wherein said electrode support means further comprises a fixation pad having two sides and having a first aperture for disengagingly receiving said distal end of said electrode.

3. A body implantable lead according to claim 2 wherein said fixation pad is of an insulating material having a second aperture positioned to permit at least partial exposure of said electrode from each of said two sides of said fixation pad.

4. A body implantable lead according to claim 3 wherein said first aperture is positioned on a first of said two sides of said fixation pad.

5. A body implantable lead according to claim 4 wherein said fixation pad further comprises surgical mesh attached to a second of said two sides of said fixation pad.

6. A body implantable lead according to claim 5 wherein said fixation pad is composed of polyether urethane elastomer.

7. A body implantable lead according to claim 6 wherein said fixation pad has an elongated rectangular shape with rounded corners.

8. A body implantable lead according to claim 7 wherein said second aperture is substantially centrally located on said fixation pad.

9. A body implantable lead according to claims 1, 2, 3, 4, 5, 6, 7 or 8 wherein said electrode has a U-shaped midportion.

10. A body implantable lead according to claim 9 wherein said distal end of said electrode has a sharp point.

11. A body implantable lead according to claim 10 wherein said conductor is a coiled wire.

12. A body implantable lead according to claim 11 wherein said proximal end of said electrode is swaged to said distal end of said conductor.

* * * * *

UNITED STATES PATENT AND TRADEMARK OFFICE
CERTIFICATE OF CORRECTION

PATENT NO. : 4,323,081
DATED : April 6, 1982
INVENTOR(S) : Wendy A. Wiebusch

It is certified that error appears in the above—identified patent and that said Letters Patent are hereby corrected as shown below:

Column 2,
    Line 64, "rencce" should be --rence--;

Column 3,
    Line 30, after "proximal" insert --end--.

Signed and Sealed this

Tenth Day of August 1982

[SEAL]

Attest:

GERALD J. MOSSINGHOFF

Attesting Officer     Commissioner of Patents and Trademarks